(12) United States Patent
Scott

(10) Patent No.: US 7,264,933 B2
(45) Date of Patent: Sep. 4, 2007

(54) METHODS TO IDENTIFY BIOLOGICALLY ACTIVE AGENTS AND SYNERGISTIC COMBINATIONS

(75) Inventor: Ian R. Scott, Mahwah, NJ (US)

(73) Assignee: Synergy Biosystems Ltd, Stratford Upon Avon (GB)

( * ) Notice: Subject to any disclaimer, the term of this patent is extended or adjusted under 35 U.S.C. 154(b) by 469 days.

(21) Appl. No.: 10/807,811

(22) Filed: Mar. 24, 2004

(65) Prior Publication Data

US 2004/0203043 A1    Oct. 14, 2004

Related U.S. Application Data

(60) Provisional application No. 60/483,564, filed on Jun. 28, 2003, provisional application No. 60/457,861, filed on Mar. 26, 2003, provisional application No. 60/457,860, filed on Mar. 26, 2003, provisional application No. 60/457,859, filed on Mar. 26, 2003.

(51) Int. Cl.
*C12Q 1/68* (2006.01)
*G01N 33/53* (2006.01)

(52) U.S. Cl. .................................... 435/6; 435/7.1
(58) Field of Classification Search ............ None
See application file for complete search history.

(56) References Cited

U.S. PATENT DOCUMENTS

| | | |
|---|---|---|
| 6,569,853 B1 | 5/2003 | Borisy et al. |
| 6,693,125 B2 | 2/2004 | Borisy et al. |
| 2002/0019010 A1 | 2/2002 | Stockwell et al. |
| 2002/0019011 A1 | 2/2002 | Stockwell et al. |
| 2002/0165261 A1 | 11/2002 | Borisy et al. |
| 2003/0078246 A1 | 4/2003 | Sackeyfio et al. |
| 2003/0096309 A1 | 5/2003 | Borisy et al. |
| 2003/0119786 A1 | 6/2003 | Kieth et al. |
| 2003/0166642 A1 | 9/2003 | Borisy et al. |
| 2004/0063769 A1 | 4/2004 | Borisy et al. |

FOREIGN PATENT DOCUMENTS

| | | |
|---|---|---|
| GB | 2242978 | 10/1991 |
| WO | WO 02/02074 | 10/2002 |

OTHER PUBLICATIONS

CTFA Dictionary, retrieved from http://www.ctfa-buyersguide.org/pls/ctfa/ctfa_bg.bg.list_ingred?p_searchtype=&p_ingred_. . . accessed Nov. 3, 2006 (2 pages).*
Eady, J. Invest. Dermatol., 101:86-91 (1993).*
Eady, Br. J. Dermatol., 131(3):331-336 (1994).*
Guy, J. Invnest. Dermatol., 110:410-415 (1998).*
Zouboulis, JEADV, 15, Suppl. 3:63-67 (2001).*
Zouboulis, Dermatol., 203:277-279 (2001).*
Harrison, Br. J. Rheumatol., 35:1096-1100 (1996).*
Alexis Borisy et al Systematic discovery of multicomponent therapeutics by Proceedings of New York Academy of Science, Jun. 24, 2003, vol. 100, part 13, pp. 7977-7982.
Spurr, E.B (2002). Rhodamine B as a systemic hair marker for assessment of bait acceptance by stoals (*Mustela erminae*), New Zealand J. Zoology, 29, 187).

* cited by examiner

*Primary Examiner*—John S. Brusca
*Assistant Examiner*—Ritesh Agrawal

(57) ABSTRACT

Methods are described using a particular type of assay system, the Multi-Pathway High Throughput Assay, in conjunction with a novel experimental strategy, whereby repeated cycles of experiments result in the identification of the most effective synergistic combinations of potential active agents from a library of materials. The novel experimental strategy not only requires far fewer total experiments than would be required using conventional discovery strategies but also maximizes the probability of finding highly synergistic combinations through the principle of multiple-pathway intervention.

26 Claims, No Drawings

METHODS TO IDENTIFY BIOLOGICALLY ACTIVE AGENTS AND SYNERGISTIC COMBINATIONS

This application claims the benefit of U.S. Provisional Application No. 60/457,859 filed Mar. 26, 2003; U.S. Provisional Application No. 60/457,860 filed Mar. 26, 2003; U.S. Provisional Application No. 60/457,861 filed Mar. 26, 2003; and U.S. Provisional Application No. 60/483,564 filed Jun. 28, 2003.

FIELD OF INVENTION

The invention relates to a method of identifying biologically active agents and combinations of such active agents that act synergistically together to create a much more potent biological response than any single active agent can achieve.

BACKGROUND OF INVENTION

Synergy among biologically active agents is a well known phenomenon. Usually the synergy is discovered either serendipitously or as a result of deduction that synergy should take place from understanding of the biological process. For example, combination of penicillin with an inhibitor of penicillinase (the enzyme that degrades penicillin) would be expected to yield a higher performing antibiotic—which indeed it does.

As scientific understanding of the complexity of living processes has increased, it has become clear that the extent to which any single biological end point is affected by many different pathways is much greater than had been expected. In particular, it has become clear that mammalian and other cells have enormous redundancy within their pathways. Nowhere has this been clearer than in the results of gene knockout experiments where the complete deletion of a gene thought to have a critical function often results in no detectable effect on the organism.

A consequence of this complexity is that many desirable biological end effects might be most easily achieved by intervening simultaneously in several pathways, and/or at multiple points within such pathways, rather than focusing on finding a single highly potent agent to act at one vital "node" within the network of pathways.

A particularly clear way to understand this phenomenon is to consider the common concept of the "rate-limiting step". Conventionally, in biology, it is believed that one step within a pathway is usually rate limiting, i.e., inhibition of that step will have immediate effect on the whole pathway while inhibition of other steps will have little or no effect. Such rate limiting steps are thus the normal target for development of drugs. Consider however what happens in a complex, highly interlinked, system of pathways. When the rate-limiting step is inhibited by an active agent, other pathways within the system compensate for that inhibition. In this new "compensated" configuration, different pathways may become rate limiting and far greater impact on the overall system will be achieved by adding an agent that acts on this new rate limiting step than would be achieved by further inhibiting the, original rate limiting step. The same logic applies when one adds a third agent to the mixture—it is likely that yet a third pathway will have become rate limiting when both of the initial rate limiting pathways have been inhibited.

This paradigm of "multiple active intervention" as source of synergy is of relevance wherever discovery of biologically effective agents is desired, including in the pharmaceutical industry. The approach is however of particular interest in the industry sectors such as cosmetics, personal care products or dietary supplements where regulatory rules do not make use of complex mixtures of active agents difficult. Of particular importance in these sectors is the potential that combinations of active agents that individually are of low potency and broad specificity might in combination be highly potent and highly selective. This property of a combination to be more potent and/or selective than expected based on the individual components is defined here as "synergy" and the mixture of ingredients displaying this synergy is what is meant as a "synergistic" mixture.

Finding such highly efficacious combinations, i.e., synergistic mixtures, of active agents is challenging however. Serendipity is not a valid route as the number of potential combinations of agents is staggeringly large. For example, there are trillions of possible 5 fold combinations of even a relatively small palette of 5000 potential agents. The other normal discovery strategy of deducing potential combinations from knowledge of mechanism is also limited in its potential for the following reasons.

Many biological end points of living organisms are affected by multiple pathways. These pathways are often not known, and even when they are, the ways in which the pathways interact to produce the biological end effect are often unknown. By biological end effect is meant the ultimate biological effect that is desired of the agent or combination, e.g., hair growth stimulation or the slowing or reversal of the skin ageing process. To further complicate the picture, many potential active agents have broad specificity (in pharmaceutical parlance they are "dirty drugs"—like aspirin) and therefore simultaneously affect multiple pathways. The mathematical tools and data banks needed to model and thus understand such complexity, do not yet exist and so use of "mechanism based" discovery of multiple synergies can rarely be achieved.

A useful but limited approach to finding highly synergistic combinations of agents was described in WO 02/02074. In this case a number of specific steps were identified within the retinol metabolism pathway, which were predicted on theoretical grounds to act synergistically with each other. Actives effective on each step were identified through highly specific assays such as enzyme inhibition and the resulting smaller set of effective compounds were tested in high order combinations. High levels of synergy were found. This approach however is limited to the special case where the pathway of interest is well understood and can thus be theoretically modeled.

There thus remains a pressing need for effective methods capable of discovering these multiple synergies, particularly those involving multiple unknown or poorly understood pathways, in a timely and cost effective manner.

A particularly significant advantage of the experimental strategy and methods disclosed herein is the increased likelihood of identifying highly synergistic combinations of biologically active materials without requiring impractically large numbers of experimental tests.

An additional advantage especially when used with the assay methods of the invention is the ability to utilize high throughput experiment methods in biological models that incorporate the multi-pathway features of real systems of interest.

A still further advantage of the strategy and methods is in the identification of highly synergistic combinations that will be suitable for use by humans.

These and other advantages will become clear from the description of the invention.

The following additional patents and publications have been considered:

Systematic discovery of multicomponent therapeutics by Alexis A. Borisy, Peter J. Elliott, Nicole W. Hurst, Margaret S. Lee, Joseph Leha'r, E. Roydon Price, George Serbedzija, Grant R. Zimmermann, Michael A. Foley, Brent R. Stockwell, and Curtis T. Keith. Proceedings of New York Academy of Science, Jun. 24, 2003, Vol. 100, part 13, pp 7977-7982. This publication describes the principles of why unpredictable biological synergy among agents is expected to occur and demonstrates the detection of binary synergies among libraries of potential drugs using a conventional method of testing all possible binary synergies between drugs in the library. 36 tests are required for each binary combination and extremely simple and ultra high throughput assays are developed to make possible the enormous number of assays needed to probe merely binary synergies within the library. No suggestion is made that more experimentally efficient strategies to discover synergies are possible and the method is clearly impractical should 3 fold or higher orders of synergy be sought because of the large number of experiments required.

GB 2242978 (Phillpot et al) describes a method for assessing materials for hair growth or pigmentation activity whereby individually microdissected hair follicles are grown in culture medium. This method is the standard method used by almost all research groups needing an in vitro hair growth assay (the patent having been abandoned). The method is however fundamentally unsuited to any high throughput application due to the laborious process of microdissecting hair follicles.

None of the references cited above teaches the specific methods to assess biologically active materials and to identify synergistic combinations as disclosed herein. The inventor is not aware of any prior art that teaches the experimental design strategy or assays disclosed herein.

SUMMARY OF THE INVENTION

The present invention describes a method for the identification of highly effective combinations of biologically active materials using a highly efficient experimental strategy that permits such combinations to be identified with far fewer experiments that would be the case using experimental strategies known in the art.

More specifically, one embodiment of the invention is a method for identifying highly synergistic combinations of biologically active agents that involves:

i. selecting a library of potential actives in which synergy is sought;

ii. identifying a subset of components S(1) which display significant activity by testing each component of the library for activity in a Multi-Pathway High Throughput Assay that targets a biological end effect for which synergy is sought, and has a known useful range of detectability;

iii. identifying a subset of binary mixtures designated S(2) that display synergy, by testing in the Multi-Pathway High Throughput Assay all or a portion of S(1) in binary mixtures with substantially each component of the library, including components that exhibited marginal or no activity in step ii), wherein the concentration of the S(1) component in the binary mixture is adjusted using a Single Component Scaling Protocol such that its activity is scaled back to a value $\lambda$ $C_{Max,1}$, where $\lambda$ is a scaling factor in the range from about 0.01 to 0.1, and $C_{Max,1}$ is the maximum activity reliably detectable at the top end of the useful range of the Multi-Pathway High Throughput Assay;

iv. optionally identifying a subset of ternary synergistic mixtures, S(3) by testing in the Multi-Pathway High Throughput Assay all or a portion of the synergistic binary mixtures S(2) in combination with substantially each component of the library, including components that exhibited marginal or no activity in step ii), wherein the concentrations of S(2) components used in the ternary mixture are adjusted using a Multiple Component Scaling Protocol or other selection criteria such that the activity of S(2) is scaled back to a value $\lambda$ $C_{Max,1}$;

v. optionally identifying a subset of N component synergistic combinations, designated S(N), wherein N is an integer greater than 3, by testing in the Multi-Pathway High Throughput Assay all or a portion of the synergistic mixtures containing (N–1) components, designated S(N–1) and identified in a manner analogous to step iv), in combination with substantially each component of the library including components that exhibited marginal or no activity in step ii), wherein the concentrations of the S(N–1) components used in this N component mixture are adjusted using the Multiple Component Scaling Protocol or other criteria such that the activity of the S(N–1) mixture is scaled back to a value $\lambda$ $C_{Max,1}$;

A second embodiment of the invention is highly synergistic mixtures identified using the experimental strategy summarized above that can be used by humans and display significant activity in a variety of biological end effects.

A third embodiment of the invention is a series of methods or assays that are used in identifying agents that display maximum biological activity targeted to the specific biological end effect. These biological end effects encompass hair growth stimulation, skin anti-ageing, dental plaque control and the resolution of acne. The assays share the common properties of being capable of use in a high through-put format as well as incorporating many of the multiple pathways that are involved in or control the actual biological end effect.

DETAILED DESCRIPTION OF THE INVENTION

The invention is based on the use of an assay system fulfilling certain critical criteria together with a novel experimental design allowing rapid identification of high order synergies.

The assay system must be capable of high throughput. The term high-throughput applies to an assay that can be automated and carried out economically at a scale greater than 100 assays per day, preferably greater than 1000 assays per day most preferably at a scale of several thousand assays per day. In conventional drug discovery, such high throughput assays are very simple and very specific. For example they may be receptor binding assays, enzyme inhibition assays and so on. In the current invention such simple assays are not suitable. The assay must incorporate enough of the whole biological system so that the multiple pathways for which synergies are sought are active and interacting in the assay. The necessary complexity of the assay varies with the target biological end effect.

For example, an assay that measures a response of a cell culture, such as proliferation or differentiation, may be satisfactory when the desired biological end effect on the whole organism is reliably predicted by the change in the single cultured cell type. Examples of such assays would be differentiation of cultured keratinocytes as an assay to predict improvement in skin condition or inhibition of triglyceride synthesis in a culture of sebocytes to predict reduction of skin oiliness.

For a more complex biological phenomenon, for example growth of hairs where hair growth is controlled by complex interactions of, inter alia, hair bulb keratinocytes and dermal papilla fibroblasts, the ideal assay would contain all the multiple cell types that interact in forming the hair. Thus an organ culture system that actually grows hair would be preferred, although simpler assays such as culture of dermal papilla cells or outer root sheath cells could be used if a synergistic set of actives was sought that acted within a single cell type of the hair follicle.

Obviously the assay must also be reproducible and sufficiently sensitive so as to have an adequate "useful range of detectability", i.e., a practical working range. It is important that this useful range of detectability, is known so as to utilize the experimental design strategy effectively. In particular, it is critical to determine the maximum activity reliably detectable at the top end of the useful range of the Multi-Pathway High Throughput Assay. This value is designated $C_{Max,1}$ Assays that are suitable as described above are called herein "MULTI-PATHWAY HIGH THROUGHPUT ASSAYS".

Experimental Design Strategy

The experimental design to utilize this assay system is distinctly different to that conventionally used in drug discovery.

It is expected that agents might be useful in the final cocktail of actives even though they have no measurable effect on their own. This is a consequence of the principals of redundancy and compensation set out in the background to the invention. Thus the experimental design that would be obvious to one with normal skill in the art—of identifying a plurality of individually effective ingredients and then performing a matrix of experiments testing all combinations of the effective agents—would miss many of the most important and effective combinations.

Instead, a novel experimental design must be used whereby:

a) A library of potential active agents is tested in the Multi-Pathway High Throughput Assay at an appropriate maximum concentration and those with significant activity are identified. The appropriate maximum concentration is relatively arbitrary and may be influenced by, for example, the cost or solubility of the particular agent. There is no need for all agents in the library to be present at the same concentration.

b) Some or all of the subset (S(1)) of actives having significant activity in the Multi-Pathway High Throughput Assay have their dose response determined in a Single Component Scaling Protocol. The term significant activity is defined here as an activity in the assay which is at least 5% of $C_{Max,1}$. This protocol is a conventional dose response study where the active is repeatedly diluted and retested in the Multi-Pathway High Throughput Assay, in order to determine the concentration at which it has a less than maximal effect. The optimum level of effect will vary with the sensitivity and variability of the assay system and may vary from about 50% to less than 1% of the maximum response found in the assay for any material tested in stage a). Thus the Single Component Scaling Protocol provides a means of adjusting the concentration of of the S(1) components taken forward such that such that its activity is scaled back to a value $\lambda C_{Max,1}$, where $\lambda$ is a scaling factor in the range from about 0.01 to 1, and $C_{Max,1}$ is the maximum activity reliably detectable at the top end of the useful range of the Multi-Pathway High Throughput Assay;

c) Some or all of the subset S(1) of actives are then tested at this minimally effective concentration in a binary combination with each chemical in the original library of potential agents at either their original tested concentration if they were inactive in step (a) or at their minimally effective concentration if they were active in step (a).

d) Those combinations of compounds giving a higher performance in the binary assay than either of the two individual components are identified as showing binary synergy and are classed as members of subset S(2).

e) Some or all of subset S(2) have dose response studies carried out using a Multiple Component Scaling Protocol to determine the concentration of components of the mixture that provide a mixture having less than maximal effect in the assay being used. The Multiple Component Scaling Protocol is a dose response study using the Multi-Pathway High Throughput Assay whereby the concentration of each component of the mixture is independently varied. For binary combinations it will produce a 2 dimensional dose response surface, for ternary combinations a 3 dimensional dose response surface and so on for higher orders of combinations. For all combinations (mixtures) other than single components there will be multiple ratios and concentrations of the components that give the same level of activity. The basis of selection of which ratio to take forward is not critical and will be influenced by the application. For example it could be the ratio that gives the lowest total concentration of actives, or the lowest combined cost of actives or the highest average clogP value (where P is defined as the octanol/water partition coefficient) or any other criteria which would be favorable in the end use envisioned. It is preferred that this Multi Component Scaling Protocol is carried out comprehensively as this will maximize the probability of finding the optimum combinations of components in the mixture, however less comprehensive protocols can be substituted provided that at least one mixture showing less than maximal effect is identified to be taken forward to the subsequent cycle. Regardless of the criteria used the key point is to scale back the activity of the combination S(2) tested such that its activity is, $\lambda C_{Max,1}$, f) Steps c) to e) are repeated, combining each chemical in the original library with the less than maximally effective concentration of the binary combinations of subset S2. This cycle can be continued indefinitely, testing the combination of each component of the library of potential actives with subset S(N−1) to identify the subset S(N) of combinations of N actives, hence identifying synergistic combinations containing any desired number of compounds, N.

Unique elements of this strategy are:
  that the concentrations of the active agents are continuously reduced as cycles are completed so that the combination of actives to which the test compound will be added has less than maximal efficacy in the assay. In other words, the strategy seeks lower concentrations of actives to achieve a given activity rather than seeking ever-higher activities.
  that candidate chemicals are not excluded from later cycles just because they proved ineffective in the initial single chemical screen or in early cycles. This requirement follows directly from the concept that multiple-pathways control complicated biological end effects.

At each stage, when the Multiple Component Scaling Protocol for the combination of actives is performed it may be found that actives that were very effective in early cycles have become marginally effective, their role being made unnecessary by the combinations of the other actives. In that case such actives may be eliminated from further cycles of testing. It is thus possible that a cycle where for example a ternary combination of agents is combined with the library of single agents that the output to the next stage will be another ternary mixture, or even conceivably a binary mixture, rather than a quaternary mixture.

Because it is possible that compounds essential at early cycles in the discovery process are no longer necessary in later cycles, it is possible to include in the original library of potential actives, compounds that are effective but cannot be used in the final compositions—for reasons such as toxicity, patent protection, regulatory constraints, cost etc. This is particularly desirable in the situation where, in the very first round of testing individual compounds, few or no effective compounds are discovered.

The strategy as set out above will require far fewer assays than would a comprehensive test of all combinations of all the candidate actives, even if every material in subset S(N) is taken forward to the subsequent cycle—see table 1. However there is a still more powerful modification to the strategy that results in even fewer assays.

In the majority of complex biological systems, the end point of interest (eg growing hair) will be controlled by a very large and highly interconnected set of pathways. In many cases this set will operate as a single highly interlinked system, in others, subsets of the larger set will exhibit particularly strong interconnections within the subset and will accordingly function as a subsystem within the larger system. Highly synergistic combinations of active agents can be discovered within each subsystem (or within the entire system if there are no effective subsystems) provided that at the end of each cycle of the strategy set out above, at least one active (or combination of actives for later cycles) acting on the subsystem is selected for progression to the next stage, where it will be combined with each member of the original library of actives. Provided sufficient cycles are completed, to the point where additional synergies are not found or are of small effect, then the most effective combination of synergistic actives will emerge at the end of the process.

Thus it is possible to select, quite arbitrarily, a relatively small number of the effective agents (or combination of agents for later cycles) from subset S(i), where i is the number of components of each subset (equal to 1–N), to take forward to future cycles. If as a result of this a compound is rejected at a particular stage, even though it would eventually have proved a vital component of the final highly synergistic mixture of actives, it will be recaptured in later cycles because every member of the library is retested at every cycle.

The number of actives that should be taken forward at each cycle is relatively arbitrary and will be governed in part by the cost and difficulty of the particular assay. In principal a single active or combination could be taken forward at each cycle but that could result in a synergistic combination of actives being found that acts only within a single subsystem, with other potentially important subsystems neglected. It is desirable therefore that a sufficient number of actives should be selected at each stage so as to make it statistically likely that every subsystem will be affected by at least one active. Thus the actual members of each subset S(1) to S(N−1) tested in combination with the full library may represent only a small number of the members of the subset. This small number might include up to about 10 and more preferably up to about 5 members.

Table 1 Illustrates the number of assays needed using the different strategies described above to discover 5 fold synergistic combinations of a library of 5000 ingredients within which 1%(50) show activity in the assay when tested as single agents and 1% show synergy at any given cycle when added to the mixture S(N) from the previous cycle.

TABLE 1

| Strategy | Number of assays | Result |
| --- | --- | --- |
| Comprehensive screen of all possible combinations of ingredients at 6 concentrations | ~$10^{22}$ | All synergies identified and the most effective synergies selected |
| Comprehensive screen of all possible combinations of agents that show activity when tested as single agents | ~$10^{8}$ | Many synergies not detected, probably including the most effective ones |
| Inventive strategy where all effective combinations are taken forward to the subsequent cycle | ~$10^{10}$ | All synergies identified and the most effective synergies selected |
| Inventive strategy where 10 effective combinations are taken forward to the subsequent cycle | ~250,000 | Many synergies identified including all the most effective synergies |

Libraries of Active Ingredients

The term "library of ingredients" is used in a broad sense to designate the collection of chemicals that is being tested employing the experimental strategy disclosed herein. The basis of choice of the library of ingredients used in the strategy will vary with the application. Non limiting examples of useful libraries include:

for applications in cosmetic products, all or part of the collection of chemicals approved for use in cosmetics in, for example the EINECS list or the CTFA dictionary of cosmetic compounds.

for pharmaceutical applications all or part of the collection of approved Rx and OTC drugs for all or a selection of indications for pharmaceutical applications all or part of the collection of candidate drugs which were not progressed through the regulatory approval process natural products including products which are themselves complex mixtures of chemicals. In the strategy described above, such complex mixtures can be treated as single members of the library Combinatorial libraries of synthesized chemicals such as those described in "A reagent-based strategy for the design of large combinatorial libraries: a preliminary experimental validation". Makara G M, Nash H, Zheng Z, Orminati J P, Wintner E A, Mol. Divers. 2003;7(1): 3-14 and in "Combinatorial chemistry and peptide library methods to characterize protein phosphatases". Vetter S W, Zhang Z Y. Methods Enzymol. 2003;366: 260-82.

While it is advisable that the entire library is used throughout the repeated cycles of the strategy it is permissible to eliminate chemicals from, or add chemicals to, the library in later cycles without invalidating the strategy.

While the detailed description above constitutes the most favored embodiments of the method, it will be clear to one skilled in the art that certain steps can be eliminated or modified without deviating from the key elements of the invention set out above and such modified methods are also claimed within this patent.

PREFERRED EMBODIMENTS OF THE INVENTION

This method of discovering high order synergies in biological systems is applicable to a wide range of biological processes including, but not restricted to, hair growth, ageing of skin or other tissues, manipulation of pigmentation, control of sebum production, treatment of dandruff, inhibition or modulation of microbial growth, stimulation of fat metabolism, modulation of inflammation, reduction of cholesterol synthesis, prevention of oxidative damage and any other biological process where a Multi-Pathway High Throughput Assay exists whose behavior is controlled by multiple biological steps or pathways. In many instances however, Multi-Pathway High Throughput Assays do not exist and must be invented to allow the strategy to be applied to a particular end benefit or biological end effect. In Examples 1-4 below, novel Multi-Pathway High Throughput Assays are described for several preferred applications of the method, i.e., biological end effects for which synergy is sought. Those novel Multi-Pathway High Throughput Assays are also claimed within this patent. Examples 5-8 describe applications of the method where Multi-Pathway High Throughput Assays already known to those of ordinary skill in the art may be used.

Use of Products Developed Using This Method

It should be understood that the products identified by the methods described herein, i.e., synergistic mixtures of biologically active ingredients, and their use to achieve specific biological end effects are also within the scope of the instant invention.

For example, in hair growth stimulation one preferred route to use the synergistic combinations identified following the methods described in detail in Example 1 is in shampoo, and hair conditioner compositions.

Shampoo compositions are well known in the cosmetic art and are generally aqueous mixtures of some or all of the following components:

surfactants which are generally mixtures of anionic, amphoteric and nonionic components (about 5% to about 20% by weight of the composition)

conditioners such as cationic polymers, silicones, oils, and cationic surfactants (about 0.5% to about 10% by weight of composition)

aesthetic additives such as perfumes, colorants, opacifiers, pearlizing agents, thickeners and suspending agents (generally less 10% by weight of composition)

Hair conditioner compositions can be either of the rinse-off or leave-on type and are also well known in the art. Such compositions generally contain:

conditioners such as water dispersible waxes, oils, cationic surfactants, nonionic surfactants, polymers, silicones (generally about 5% to about 25% by weight of composition, styling aides such as various water soluble film forming polymers, insoluble polymers and latexes (generally less than about 5% by weight of composition)

aesthetic additives such as perfumes, colorants, opacifiers, pearlizing agents, thickeners and suspending agents (generally less 10% by weight of composition)

A description of the formulation of shampoo compositions is given by Wells in U.S. Pat. No. 5,573,709 incorporated by reference herein. A description of the formulation of hair conditioning compositions is given by Ansher-Jackson et al in U.S. Pat. No. 5,100,657 incorporated by reference herein.

EXAMPLES

The following examples are shown as illustrations of the invention and are not intended in any way to limit its scope.

Example 1

Hair Growth

A particularly preferred application is the biological end effect of hair growth. Hair growth is a complex phenomenon. Several pathways are already known to influence hair growth and it is highly likely that many other, as yet undiscovered, pathways are involved. It is therefore a biological system likely to be amenable to highly synergistic combinations of active ingredients.

Multiple-Pathway High Throughput Assays Targeting Hair Growth

There are many references in the scientific literature to methods measuring the effect of active agents on hair growth. The most validated method involves the use of living animals with agents applied topically or provided systemically. In vitro systems to measure the effect of agents on hair growth have, in contrast, been challenging to develop. The most successful systems have involved the manual dissection of single hair follicles, either from rodent vibrissae or from human skin (see Philpott, GB 2 242 978A). In both cases the procedure is laborious and as a result the number of potential active agents that can be tested is very limited. In principle, culture of small biopsies of skin that contain intact hair follicles could be capable of higher throughput of potential actives. However, attempts to culture skin in this way using normal "organ culture" systems have failed because the hair follicle has failed to maintain a normal growth pattern for longer than a few days (eg Li L, Margolis L B, Paus R, Hoffman R M, Hair shaft elongation, follicle growth, and spontaneous regression in long-term, gelatin sponge-supported histoculture of human scalp skin. Proc Natl Acad Sci USA. 1992 Sep. 15;89(18):8764-8.).

Other potential in vitro systems include culture of dermal papilla cells or hair follicle keratinocytes but, while practical and capable of high throughput, these systems fail to mimic the complexity of the intact hair and as such are prone to many false positive and false negative results.

Culturing of small pieces of intact skin under standard conditions is a well established technique in bioscience. Normally the skin is cut with a keratotome to a thickness of about 0.5 mm before being placed into culture, otherwise the limited diffusion of nutrients through the thick dermal layers results in loss of growth or even necrosis of the epidermal layers. Thus these methods have been of no value in growing intact hair follicles as the keratotome step cuts through the follicle. As stated above, attempts to culture full thickness skin result in quite rapid loss of organized growth of the hair follicles, perhaps due to inability of nutrients to penetrate to the hair follicle in sufficient quantities.

Low Temperature Whole Skin Organ Culture.

It has been surprisingly found that this limitation can be overcome by simply culturing small pieces of full thickness skin in standard growth media at reduced temperature, the follicles continuing to grow with normal architecture for many days. The temperature of culture must be reduced below the standard culture temperature of 37 degrees C., to at least 30 degrees and preferably to 20-25 degrees or even lower temperatures. This method of culturing hair follicles within whole pieces of skin, and the associated measurement techniques described below is referred to as "Low Temperature Whole Skin Organ Culture".

Without wishing to be bound by theory, it is believed that the basis for this phenomenon lies in the different effects of temperature on the processes of cell growth and respiration (where a small decrease in temperature has a large effect on the rate of growth and respiration) and of the diffusion of small molecules through the skin (where the temperature dependence is much less). Thus at lower temperatures the less metabolically active hair follicles do not over-deplete the nutrients available to them from diffusion from the culture medium.

This key innovation allows cultures of whole pieces of skin containing one or more hair follicles to be sustained long enough for actives that modulate the growth of the hair to be evaluated—typically, 3-10 days.

Preferred Embodiments of the Method Include
1) Reducing the temperature of the culture to below about 30 C as described above.
2) The use of serum free growth medium such as Dulbecco's Modification of Eagles medium or Williams E medium to minimize the phenomenon of epiboly wherein the epidermal layers grow to fully enclose the skin sample (see Stenn K S, Dvoretzky I. Human serum and epithelial spread in tissue culture. Arch Dermatol Res. 1979 Feb. 23;264(1):3-15.)
3) Removal of the superficial layers of the skin comprising the epidermis and part of the hair follicle above the sebaceous gland prior to culturing the skin. This can be easily achieved using a keratotome set at about 0.2 mm. The result of this is increased area for nutrient diffusion into the skin and reduced consumption of nutrients by the actively growing epidermal keratinocytes. Under these conditions hair follicle growth is sustained for longer times or with fewer changes of medium
4) Use of small pieces of skin containing only one or a few follicles—typically between 1 mm and 6 mm in diameter. Use of such small pieces of skin results however in a significant proportion of the hair follicles being damaged because the follicles typically do not lie perpendicular to the skin surface and many follicles whose upper parts lie within the skin piece have their lower portions transected by the cut surface of the skin piece. This problem can be mitigated by use of one of three novel cutting devices described below which provides a cut surface which is much more likely to be in a direction parallel to the follicle and thus much less likely to dissect the follicle below the subaceous gland;
   a. The novel skin cutting device consists of a series of sharp blades separated by a gap of 1-8 mm, held at either a set angle or an adjustable angle to the vertical and contained within a holder. The assembly of blades can be driven into a piece of skin either manually or by a power operated press, preferably with the force of the press aligned parallel to the blades in the device. A second similar device is then used to cut the strips of skin at right angles to the first cut and with a blade angle selected to minimize follicle damage. It will normally be possible to align the piece of skin being cut so that the first cut is made at an angle of around 30 degrees from the vertical (depending on the source of the skin) while the second cut can be vertical. A simple and preferred example of this device involves threading standard or large razor blades onto two threaded metal rods with slightly oversize washers between each blade to provide the 1-6 mm spacing. The blades and washers are then clamped together by tightening wing nuts at each end of the rod. The angle of the blades, if not at 90 degrees to the rods, is set by threading shaped inserts onto the rods between the outermost blade on each end and its associated wing nut.
   b. The novel cutting device is similar to that described in a) but replaces the razor blades with circular cutting wheels, mounted on a supporting rod and with similar shaped inserts assembled at each end of the rod to tilt the circular blades to the desired angle.
   c. The novel skin cutting device consists of a set of circular biopsy punches of diameter 1-8 mm set into a frame at a fixed angle from the vertical such that when driven into the skin sample, the punches cut parallel to the direction of the hair follicle.

In all of the cutting devices described it is advantageous to place a sheet of soft wax or plastic below the skin to prevent damage to the cutting edges when they cut through the skin.

In a sentence, the Low Temperature Whole Skin Organ Culture is a miniaturized culture of skin that contains intact viable hair follicles below the sebaceous gland, ideally has a significant portion of the epidermis removed, and is maintained in a serum free growth medium at a temperature below about 30 C and whose hair growth is measured by a high-throughput technique.

High-throughput Hair Growth Measurement Technique

In any in vitro method for evaluating the effect of substances on hair growth it is necessary to measure the hair growth rate with sufficient accuracy to detect an effective candidate biological active. Many methods have been used with success in the past. These include measuring increase in length microscopically and measuring incorporation of radio-isotope labeled amino acids. Measuring hair growth in a culture of full thickness skin is challenging however as direct microscopic examination is difficult and far too laborious for any high throughput application and radioisotope incorporation is confounded by incorporation of isotope into structures other than the hair.

An additional aspect of this method therefore is the development of a number of novel measurement tools suitable for use on hair growing within whole skin pieces and capable of use in a high throughput modality. Specifically three methods of measurement described below satisfy these requirements:
1) At the end of the culture experiment the skin biopsy can be dissolved using either a sequential or concurrent exposure to a mixture of proteases preferably including collagenase. This method can be used on whole skin but is particularly effective when the epidermis has been removed prior to the culturing experiment (see preferred embodiment 2 above). Optionally this step can be combined with dissolution of the partly dissolved skin in hot sodium dodecyl sulphate combined with a reducing agent such as dithiothreitol or 2 mercaptoethanol. At the end of this procedure the hair shaft remains intact and can be measured for length and diameter using a microscope and standard image analysis software tools. This method is well suited to automation by standard robotic systems as all digestion stages can be carried out in multiwell plates and soluble extracts removed by standard pipetting tools. The residual hair can be microscopically examined in situ in the multiwell plate using an automated stage to move the microscope from well to well. The effect of the potential hair growth active is determined by comparison of the final hair length in the test assay in comparison with a control assay lacking the active.

2) It is known that fluorescent dyes such as rhodamine have been used as markers in bait to determine when wild animals eat the bait. The dye, once ingested is incorporated into the growing hair so that the position of the fluorescent dye along the hair shaft indicates the time since the animal ate the bait (Spurr, E. B (2002). Rhodamine B as a systemic hair marker for assessment of bait acceptance by stoats (*Mustela erminae*), New Zealand J. Zoology, 29, 187). This phenomenon is applied to the problem of measurement of hair growth in vitro by adding a fluorescent dye that is tightly incorporated during the formation of the growing hair to the culture medium while the hairs are growing. Suitable dyes include, but are not limited to, Rhodamine B (preferred), rhodamine 6G and rhodamine 110. The dye can either be added continuously to the culture so that the entire length of hair produced in culture is labeled, or the dye can be added in pulses so that the hair shows bands of fluorescence, the separation of which indicates how much hair growth occurred between exposures to the dye. In either case it is necessary to isolate the hair from the skin in which it is embedded in order to visualize the fluorescent zones in the hair using fluorescent microscopy. This separation can be carried out using any of the methods set out in 1) above. In certain cases, weak binding of the fluorescent dye to the existing hair shaft may occur but this weakly bound dye can easily be removed by washing the hair with a mild surfactant solution 3) Growing hairs can be labeled with radioactive amino acids and isolated at the end of the culture period by the methods set out in 1) above. This latter procedure obviates the interference by radioisotope incorporation in tissue other than the hair fiber.

Isolated Hair Follicle Assay

As stated above, the isolated hair follicle assay described by Phillpot (GB 2 242 978A) is an excellent model for measuring the effect of potential actives on hair growth, but is of limited utility for the application described herein because it is incapable of scaling up to high throughput formats. There are three reasons for this. Firstly, as described, the isolation of individual hair follicles is slow and laborious making isolation of sufficient follicles for a high throughput assay problematical. Secondly, measurement of growth of the hair in such cultures is also problematical. Direct measurement of elongation of the hair by microscopic examination is an excellent method but is too slow and labor intensive for routine use in a high throughput format, involving as it does multiple repeated measurements of the length of each individual hair follicle. Incorporation of radioactive thymidine is convenient but is not able to distinguish organized from disorganized growth of the hair and is thus unreliable. The same concern applies to incorporation of other radioisotopes such as amino acids. Thirdly, the published methods are restricted to sources of hair follicles that are intrinsically restricted, either rodent vibrissae (which are restricted in number) or human skin (which is restricted in availability and very variable). None of the published methods is suitable for isolating follicles in large numbers from easily available skin sources such as rodent dorso-lateral skin or pig skin.

Hair follicles can be isolated in large numbers from normal skin, including rodent dorso-lateral skin and pig skin, by the following novel procedure described herein as an alternative to individual dissection. In skin where the hair bulb does not protrude below the dermis into the subcutaneous fat, the subcutaneous fat is removed by scraping or other appropriate method. The skin is then cut horizontally using an appropriate instrument such as a keratotome, at a depth such that the hair is transected sufficiently far above the hair bulb so as to leave the hair bulb intact with at least approximately 2 mm of hair shaft attached. The remaining dermis is then treated with a solution of collagenase for sufficient time to loosen the follicles from their attachment to the residual dermis. This can be readily observed when follicles can be loosened from the residual dermis by gentle probing with forceps.

When the follicles have been loosened, the dermis is gently dispersed using any of a number of low shear methods including but not restricted to use of a blade homogenizer on low speed, use of a tube and plunger type homogenizer with a large gap between tube and plunger, low frequency ultrasonic dispersion or manual rubbing of the dermis against an appropriately sized sieve.

The isolated follicles are then separated from the residual dermis by sieving or by differential or density gradient centrifugation or can be left mixed with the residual dermis.

The isolated follicles are transferred to wells of a multiwell dish. A preferred rapid technique is to suspend the follicles in culture medium with stirring and to aliquot samples of follicles using a wide tipped automatic pipetting system to each well so that each well contains a plurality of follicles. The follicles are grown under standard conditions such as those described by Philpott (as a non restrictive example, Williams E medium at 37 degrees C.).

Follicles prepared in this way are significantly more contaminated with other skin tissues than is the case with micro-dissection. This makes measurement of hair growth more difficult. Automated microscopic examination is complicated by the presence of extraneous pieces of tissue. Isotope incorporation is confounded by variable uptake of isotope into extraneous tissue. However, use of the techniques described above under "measurement of hair growth" and in particular the use of Rhodamine or related fluorescent dyes overcomes these difficulties and makes the assay suitable for high throughput applications.

In a sentence, in the Isolated Hair Follicle Assay individual follicles are removed from sectioned dermis in a viable state through the action of collagenase followed by gentle dispersion, are cultured in a suitable growth medium and their hair growth measured by a technique capable of high throughput and not affected by the presence of contaminating tissues in the culture.

Libraries for Hair Growth Stimulants

In the context of hair growth it is desirable to include prescription drugs such as finasteride, minoxidil, vitamin D analogues and retinoic acid, that are known to have hair growth activity, in the original library even though such materials may not be usable in the final cocktail of actives. The presence of these potent agents in early cycles of the method will result in a greater number of synergies being discovered, some of which may prove strong enough to allow removal of the prescription drug from the final cocktail without complete loss of activity.

A preferred library of candidate chemicals is one selected from chemicals known within the personal care and pharmaceutical industries as being safe for use, and hence requiring little or no additional toxicology experimentation prior to sale. Lists of suitable chemicals can be selected from the European EINECS list and the Cosmetic Toiletries and Fragrance Association Dictionary of Cosmetic Ingredients. The library of compounds can also contain individual items which are actually mixtures of multiple chemicals, for example mixtures of isomers, chemical reaction products containing multiple chemicals or complex natural products such as plant extracts.

A further preferred library of candidate ingredients is that subset of the 10$^{th}$ Edition of the CTFA Dictionary of Cosmetic Ingredients identified by cross reference within the CD ROM version of the Dictionary as having any form of biological activity.

A further preferred library of candidate chemicals includes those chemicals which, from current admittedly incomplete knowledge of pathways influencing hair growth might be expected to have potential for modulation of hair growth. These include the following classes, a) to f).

a) Retinol or its esters, optionally combined with agents such as those described in WO 02/02074 (retinol boosters), the teachings of which are incorporated by reference into the present application.
b) The complexes of Copper ions with short peptides as described in U.S. Pat. No. 6,017,888 and especially the hydrophobic or hydrophobically modified peptides referenced therein
c) Minoxidil, melatonin, ketoconazole, fenugreek extract, phospatidic acid and zinc pyrithione
d) Natural products providing anti hypertensive activity including but not limited to:
   Hawthorne, Arjuna bark, Olive leaf, European mistletoe, Yarrow, Black cumin seeds, Nigella sativa, Forskolin, Indian Snakeroot, Garlic, Coenzyme Q10 Omega 3 fatty acids and their esters and glycerides, ginseng extract
e) Natural products containing antiandrogens including but not limited to:
   Saw Palmetto, Stinging nettle (urtica dioica)
f) Chemicals capable of binding to the vitamin D receptor including lithocholic acid
g) agonists (activators) of the Hedgehog signaling pathway as described in U.S. Pat. No. 6,639,051

Hair growth products can be in many forms—topical scalp lotions are most common but for sufficiently potent active systems incorporation into shampoos or conditioners would be advantageous. For actives to deliver adequately to the scalp from such rinse off compositions it is preferable for them to be very hydrophobic, ideally with an octanol water partition coefficient higher than 100 (ie a clog P>2), and more preferably higher than 1000 (clog P>3). Accordingly, a selection criterion for both the original library of compounds and for which compounds to progress through the multiple cycles of the method can be partition coefficient. This selection criterion can be formalized as requiring a high (e.g., >1000) octanol/water partition coefficient when the actives are to be formulated into a rinse off product and can be applied not only to the methods described within this application but also to synergistic active systems discovered through other methods, e.g., those described in WO 02/02074.

Specific examples of the general method of this example are given in the table below

| Element | Ex 1A | Ex 1B | Ex 1C |
|---|---|---|---|
| Library | Entire CTFA Dictionary | CTFA Dictionary | Actives selected from knowledge |
| Additional inclusion requirement | None | Known to have biological activity | of hair growth control mechanisms |
| Approx size of library | 12000 | 2000 | 200 |
| High-Throughput Multi-Pathway Assay | Low Temperature Whole Skin Organ Culture | Isolated Hair Follicle Assay | Low Temperature Whole Skin Organ Culture |
| N | 4 | 6 | 5 |
| λ | 0.1 | 0.3 | 0.2 |
| Number of S(i) mixtures taken forward | 5 | 10 | 10 |
| Total number of experiments (range) | ~300,000 | ~120,000 | ~10,000 |

Example 2

Treatment of Ageing Skin

Regeneration of aged skin is a complex process that involves reciprocal interactions between dermis and epidermis. Successful regeneration involves changes in both dermal and epidermal compartments. Thus for a model system to have the best possibility of predicting clinical benefit, the model should contain both epidermis and dermis and measurements of the effects of actives on both compartments should be possible.

To date, no high throughput method fulfilling these criteria has been published. Organotypic cultures where fibroblasts and keratinocytes are grown together on a suitable support have been developed and scaled up to industrial scale. The high price of such cultures is however prohibitive for high throughput applications and, in any case, the relevance of changes in the very artificial dermal matrix is questionable.

Organ culture of skin is a well established technique and cultures can be maintained for many days. Such cultures are thus the system of choice for testing the effect of antiaging actives. However, there are no reports of anyone successfully scaling up such organ cultures to the several thousand a week needed for high throughput applications. The obstacles are two fold. First is the difficulty of actually preparing large numbers of such cultures. Typically the pieces of skin are manually placed onto special supports in relatively large tissue culture plates, a technique that is hard to scale up. Secondly there is the difficulty of measuring changes in the cultured skin. The ideal method for doing so is histology but with conventional methods of histology that would be impossible to scale up to high throughput scale.

Two novel methods have been devised to overcome these problems and permit use of organ cultures analysed by histology at high throughput. These assays are described below.

Multi-Pathway High Throughput Assays Targeted to Skin Anti-Ageing

High Throughput Histology Organ Culture Assay
i. Cut skin with a keratotome or dermatome so that the skin consists of complete epidermis and a sufficient amount of supporting dermis. Cut this keratotomed skin into small pieces using a suitable apparatus and transfer single pieces to 96 well plates preferably using a suction device to pick up and transfer several skin pieces simultaneously. A preferred device for this stage is a set of razor blades or sharpened disks similar to that described for the Low Temperature Whole Skin Organ Culture assay where the blades or disks are spaced at 3 mm. When skin is cut twice at right angles with this device, 3 mm squares of skin are produced in an array such that every $3^{rd}$ square is in register with the position of the wells on the 96 well plates, which are spaced with 9 mm centers. Rapid transfer of many pieces directly into 96 wells plates with the aid of a suction device is then facilitated.

ii. Culture the skin pieces with a suitable, preferably serum free, medium. In a preferred embodiment, the stratum corneum surface of the keratotomed skin is made to adhere to a layer of material that is lighter than water—eg wax, plastic foam etc—prior to its being cut into pieces. The individual pieces then float on the culture medium by virtue of this light layer of material.

iii. At the end of the culture period remove the skin pieces from the wells of the culture plate, preferably using a suction device to pick up several skin pieces at once and transfer them to a suitable mold in which they can be stacked into either 12 columns of 8 pieces or 8 columns of 12 pieces.

iv. Process all 96 pieces, while still mounted in the mold, conventionally for histology so that all 96 pieces are ultimately mounted in single block (paraffin or other mounting material)

v. Microtome sections off the resulting block so that each microtomed section contains cross sections of all 96 skin pieces vi. Process the sections for histology, histochemistry or immunohistochemisty so as to detect relevant markers of skin regeneration, e.g., increased epidermal thickness, restoration of normal basement membrane architecture, deposition of new collagen, etc.

vii. Examine the resulting microscope slides using an automated microscope with a motorized stage and appropriate image analysis software.

In a sentence High Throughput Histology Organ Culture Assay entails a viable culture of miniature pieces of epidermis with at least a portion of associated dermis in a multiple well assembly, followed by the embedding of large numbers of cultured skin pieces in a single block and histological sectioning of the entire assembly and the automated histology, histochemistry or immunohistochemisty of histological sections carried out in a high throughput manner.

Topical Application High Throughput Histology Organ Culture Assay i. Use a keratotome or dermatome to cut sheets of skin containing the complete epidermis and sufficient supporting dermis ii. Using silk screen or other appropriate method apply a silicone or other appropriate compound to the skin surface so as to segment the surface into separate areas of skin separated by silicone barriers with the resulting pattern matching that of the wells in a standard 96 or 384 well tissue culture plate.

iii. Mount the resulting skin on a frame such that it can be floated intact on tissue culture medium iv. Apply test compounds, dissolved in a suitable vehicle such as an ethanol/polyol mixture, to the surface of the skin using an automated pipetting system. This step may be repeated during the course of the culture.

v. After the culture period is complete, cut the skin into strips containing 8 or 12 treatment sites and stack the strips on top of each other. Process this assembly for histology as a single large sample and analyze histologically as in the High Throughput Histology Organ Culture Assay.

This second method has the considerable advantage that it incorporates the transdermal delivery of the active materials into the assay and will therefore be more likely to predict clinically effective formulations.

Thus, the Topical Application High Throughput Histology Organ Culture Assay is a culture of a sheet of viable epidermis and associated dermis, partitioned into a pattern of isolated regions to which different test solutions can be topically applied, by the application of a surface barrier film, followed by the embedding of large numbers of cultured skin pieces in a single block and histological sectioning of the entire assembly and the automated histology, histochemistry or immunohistochemisty of histological sections carried out in a high throughput manner.

Library

A preferred library for this example is the subset of the $10^{th}$ Edition of the CTFA Dictionary of Cosmetic Ingredients identified by cross reference within the CD ROM version of the Dictionary as having any form of biological activity.

Example 3

Anti Acne

Acne is a complex and multifactorial condition. Two of the most critical factors are believed however to be growth of P. Acnes and the blockage of the follicle duct by hypercornification of the follicular stratum corneum under the influence of Interleukin 1 alpha (IL1) (see *Assessment of etiologic agents in acne pathogenesis*. Burkhart C N, Gottwald L. Skinmed. 2003 Jul-Aug;2(4):222-8 and *Modeling the infundibulum in acne*. Guy R. Kealey T. Dermatology. 1998; 196(1)). Neither of these factors are easily modeled in a high throughput mode however.

In the case of P. Acnes, while measurement of growth inhibition by conventional bacteriological methods is straightforward such methods are very poor indicators of clinical benefit. Two factors combine to make this so—the fact that in vivo P. Acnes grows in a unique sebum filled environment and that the bacterium is physically located deep in a narrow, sebum filled duct in the skin, making access of the antibacterial active to the bacterium far from easy.

Multi-Pathway High Throughput Assays Targeted to Acne Resolution or Control

Simulated Follicle P. Acnes Assay

A novel assay that overcomes both of these problems is to inoculate P. Acnes (or other organisms) into synthetic sebum and pump the inoculated sebum into a narrow plastic tube of diameter similar to the follicular duct. The filled tube is then cut into lengths of 2-8 mm which are placed into wells of a multiwell dish (96 or 384). The tube segments are exposed to actives incorporated into formulations that can mimic what will be used clinically, e.g., rinse-off formulations with surfactants such as shampoos. After the desired period of exposure the tube segments are rinsed and incubated to allow growth of the surviving bacteria. The bacteria are extracted from the tube using a solvent that dissolves the synthetic sebum. The number of bacteria is then estimated using a standard method such as DNA fluorescence.

In a preferred embodiment of this assay, P Acnes purchased from the National Type Culture Collection are seeded into a synthetic sebum of 50% triglyceride, 20% squalene, 10% cholesterol, 10% free fatty acid, 5% water and 5% hydrolysed casein at a density of 100,000 per ml. The resulting suspension is pumped into standard plastic HPLC tubing. 3 mm sections of the tubing are cut using a rotating knife blade linked to a motorized reel containing the tubing and the sections of tubing dropped into 96 well plates. Aliquots of the test agents, dissolved in a 10% solution of a facial wash product are introduced to the wells for a period of 1 minute to simulate normal washing conditions and then removed. The wells are rinsed in sterile water and then saline is added to maintain hydration of the sebum in the tube segments. The plates are incubated at 37 degrees for 24 hours and the saline is removed and replaced with 66% hexane, 33% ethanol. The plates are shaken on a rotary shaker for 2 hours by which time the sebum has dissolved and the bacteria are present in suspension in the solvent.

An aliquot of the resulting suspension is taken and diluted into 1% triton X100. Pico green dye is added as described in 'Characterization of PicoGreen reagent and development of a fluorescence-based solution assay for double-stranded DNA quantitation'. Singer V L, Jones L J, Yue S T, Haugland R P. Anal Biochem. 1997 Jul. 1;249(2):228-38 and the DNA content determined by measurement of fluorescence.

Thus, the Simulated Follicle P. Acnes Assay is a culture of P. Acnes dispersed in a synthetic analogue of human sebum and held within pieces of tubing of dimensions similar to the sebaceous duct, that is exposed to antibacterial agents under realistic conditions and where growth of the surviving P. Acnes is measured by a high throughput method such as DNA fluorescence.

Inhibition of IL1 Induced Hypercornication Assay

In the case of IL 1 induced hypercornification very similar assays to the two described under the example "treatment of ageing skin" can be used, with the key difference that a (just) sufficient amount of IL1 to induce hypercornification is added to the culture medium. The extent of hypercornification is determined by high throughput histology and automated microscopy exactly as for antiaging except that a cornification marker is used such as change in the dye binding properties of the stratum corneum. As non-limiting examples, staining with eosin shows hypercornified stratum corneum as a deeper red than normal stratum corneum. Alternatively one can measure loss of the granular layer, detected by immunostaining with an antibody to profilaggrin (Scott IR, Harding C R: *Filaggrin breakdown to water binding-compounds during development of the rat stratum-corneum is controlled by the water activity of the environment. Dev Biol* 115: (1) 84-92 May 1986)

In either case, the measured end point is then the reduction by an applied active of the extent of IL1 induced hypercornification.

Thus, the Inhibition of IL1 Induced Hypercornification Assay entails either (i) a viable culture of miniature pieces of epidermis with at least a portion of associated dermis in a multiple well assembly, or (ii) a culture of a sheet of viable epidermis and associated dermis, partitioned into a pattern of isolated regions to which different test solutions can be topically applied, by the application of a surface barrier film; in either case using a culture medium containing a level of IL1 sufficient to cause hypercornification; followed by the embedding of large numbers of cultured skin pieces in a single block and histological sectioning of the entire assembly and the automated histology, histochemistry or immunohistochemisty of histological sections carried out in a high throughput manner.

Library

A preferred library for this example is the subset of the 10$^{th}$ Edition of the CTFA Dictionary of Cosmetic Ingredients identified by cross reference within the CD ROM version of the Dictionary as having any form of biological activity.

Example 4

Dental Plaque

While dental plaque is essentially microbial in origin, conventional microbiological assays fail to accurately predict the effect of an oral product in inhibiting growth of plaque. This is in part at least due to the fact that in dental plaque the microbes grow as a biofilm in a complex matrix that both reduces access of the antimicrobials to the microbes and changes the biochemical behavior of the microbes so that they respond quite differently to the antimicrobial agent than they would if they were growing planktonically, i.e., free in suspension. Efforts have been made to create accurate models of dental plaque and the most successful have been plaque films grown under chemostat conditions with continuous flow of medium over the plaque (see *Chemostat flow cell system: an in vitro model for the evaluation of antiplaque agents.* J Dent Res. 1994 November;73(11):1748-55) Herles S, Olsen S, Afflitto J, Gaffar A. Such models have been proved to be superior predictors of clinical benefit but have been far too cumbersome to scale up to high throughput.

Multi-Pathway High Throughput Assays Targeted to Dental Plaque Control

The Plaque Biofilm Regrowth Assay

A novel way to achieve high throughput in such assays is to replace the use of a chemostat by regular removal and replacement of a fraction of the medium in a 96 or 384 well plate using an automated pipettor. Flow of the medium over the growing plaque can be simulated by gentle rotary shaking or tilting of the multiwell plate. The medium can either be fresh sterile medium or can be the output of a larger conventional chemostat, stored at low temperature until needed, that can contain planktonic microorganisms. The plaque biofilm can either be allowed to grow on the surface of the plastic plate or on a hydroxyapatite insert or layer of hydroxyapatite coated on the plastic surface.

A further modification of this method allows easy simulation of the normal conditions of plaque growth in the mouth, i.e., that nutrients are available at high concentrations but only for short times, i.e., at and after meals. The use of the robotic pipettor as envisioned above makes it easy to "pulse" the growing plaque with nutrients at whatever frequency is desired. Such robotic pipettors are available from a variety of manufacturers. A particularly suitable example is the Genesis RSP available from Tecan US, P.O. Box 13953, Research Triangle Park, N.C. 27709, USA, which can be used in combination with the TRAC system allowing automated transfer of plates from the pipettor to and from an incubator.

A preferred way to use these cultured plaque biofilms in an assay for prevention of dental plaque growth is to allow the biofilm to fully develop as described above and then to partially remove it with mechanical abrasion in the presence of a diluted dentifrice or other oral care product containing the active(s) of interest. This can simulate actual use conditions. Partial removal can be achieved by, for example, scraping a defined area free of plaque using a scraping tool. Alternatively, if a groove is fabricated in the surface on which the biofilm grows, then the surface can be comprehensively cleaned using a mechanical rotary brush, leaving plaque only in the protected groove. In either case, after rinsing away the test product, the biofilm is exposed again to growth medium (optionally with the same regular changes of medium as when it was grown) and the time for the plaque biofilm to grow out from the protected groove or to fill in the area from which plaque was removed is the measure of the efficacy of the tested agent. This is easily measured by staining the biofilm with a dye—such as that used in oral disclosing products—and scanning the plate with an automated microscope or, more simply, using a conventional flat bed scanner. The usual dye used is D&C Red 28 and can be purchased ready for use in products such as Plaque-Finder™ from Professional Dental Technologies, Inc. P.O. Box 3749, Batesville Ark. 72501.

Automated image analysis of the resulting image to detect the dyed area and intensity provides a quantitative measure of plaque regrowth.

Should repeated measures of the progression of plaque biofilm regrowth be desired, the use of the dye can be avoided by visualising the plaque by an optical contrast method such as phase contrast microscopy.

Thus, The Plaque Biofilm Regrowth Assay involves the growth of a plaque biofilm in multiwell plates preferably under conditions of medium replenishment approximately simulating chemostat conditions, followed by the partial removal of the biofilm using mechanical abrasion in the presence of the test agents and detection of the rate of regrowth of the biofilm, optionally using a disclosing agent, via automated image detection and analysis.

Library

A suitable library of ingredients for use in this example comprises agents with known antibacterial effect selected from the CTFA Dictionary of Cosmetic Ingredients, polymers capable of binding to hydroxyapatite such as Gantrez, surfactants that can disrupt membrane function, inhibitors of energy metabolism such as sodium fluoride, inhibitors of carbohydrate synthesis and natural products believed to be effective antiplaque agents such as extract of neem root.

Example 5

Hygeine

Synergistic combinations of actives effective in killing or prevention of growth of microorganisms are easily discovered using the strategy described in this application. Standard high throughput microbiological assays can be used with little modification. In a preferred example, a library consisting of all preservatives and biocides listed in either EINECS or CTFA Dictionary of Cosmetic Ingredients, together with plant extracts reported to have microbial activity and surfactants is used. The actives or combinations are dissolved in a diluted formulation designed to mimic the ultimate product while in use. Relevant microorganisms are added to the mixture of actives in the diluted formulation and incubated for a time similar to that to which the organisms would be exposed during typical product use. At the end of the time period, small aliquots of the mixture are diluted by at least 20 fold in microbial growth medium and the resulting mixture incubated to allow the surviving microorganisms to grow. An inactivator containing for example a hydrophobic solvent or emulsifier can also be employed. The turbidity of the mixture is measured at intervals and the delay in reaching a given turbidity, compared to a control experiment where no antimicrobial actives were used, is a measure of the inhibition of microbial growth achieved. This entire assay is conveniently carried out in 384 well plates with automated 96 or 384 channel pipetting systems.

Example 6

Deodorancy

Body and underarm odor are caused by the action of microorganisms on bodily secretions, particularly apocrine gland secretions. Conventional microbiological assays can be used to discover synergistic combinations of actives that kill or inhibit the growth of the relevant microorganisms.

Example 7

Inhibition of Sebum Production

Synergistic mixtures of ingredients capable of reducing sebogenesis by the sebaceous glands of, for example, the face and thereby reducing the severity of facial oiliness can be identified using the method of this patent, a library of biologically effective ingredients from the CTFA Dictionary of Cosmetic Ingredients and a high throughput assay based on that described by Harirchian et al in US 20040018948 where secondary cultures of human sebocytes are exposed to the agent or mixture of interest in the presence of radiolabelled acetate and the incorporation of radiolabelled acetate into triglycerides is measured during differentiation of the sebocytes.

What is claimed is:

1. A method for identifying highly synergistic combinations of biologically active agents comprising:
  i. selecting a library of ingredients to be tested as potentially biologically active agents in which synergy is sought, said ingredients being designated as components of the library;
  ii. identifying a subset of components S(1) from the library which display significant activity by testing each component of the library for activity in a Multi-Pathway High Throughput Assay said assay targeting a biological end effect for which synergy is sought;
  iii. carrying out a Single-Component Scaling Protocol on one or more of the S(1) components identified in Step (ii), wherein the one or more S(1) component is repeatedly diluted and retested in the Multi-Pathway High Throughput Assay, and determining a concentration at which its activity in said assay is $\lambda\, C_{Max,1}$, where $\lambda$ is a scaling factor in the range from about 0.01 to 0.5, and $C_{Max,1}$ is the maximum activity measurable in said assay;
  iv. identifying a subset of binary mixtures designated S(2) that display synergy, by testing in the Multi-Pathway High Throughput Assay all or a portion of S(1) components in binary mixtures with substantially each component of the library, including components that exhibited marginal or no activity in step ii), wherein the concentration of each S(1) component in the binary mixture is the concentration found in step iii to have an activity $\lambda\, C_{max,1}$;
  v. carrying out a Multi-Component Scaling Protocol on one or more of the S(2) binary mixtures identified in Step (iv), wherein the concentration of each component of the one or more S(2) binary mixture is independently varied and the activity of the mixture is measured in the Multi-Pathway High Throughput Assay and determining concentrations for each of the components of the one or more S(2) mixtures at which the activity of said mixture in said assay is $\lambda$ $C_{Max,1}$;

vi identifying a subset of ternary synergistic mixtures, S(3) by testing in the Multi-Pathway High Throughput Assay all or a portion of the synergistic binary mixtures S(2) in combination with substantially each component of the library, including components that exhibited marginal or no activity in step ii), wherein the concentrations of each of the S(2) components used in the ternary mixture is the value found in step v that provides the S(2) mixture with an activity in said assay of $\lambda$ $C_{Max,1}$;

vii. carrying out a Multi-Component Scaling Protocol on one or more of the S(3) mixtures identified in Step (vi), wherein the concentration of each component of the one or more S(3) mixture is independently varied and the activity of the mixture is measured in the Multi-Pathway High Throughput Assay and determining concentrations for each of the components of the one or more S(3) mixtures at which the activity of said S(3) mixture in said assay is $\lambda$ $C_{Max,1}$ and determining whether any component of each ternary S(3) mixture may be eliminated in further testing cycles because it has become marginally effective in the ternary mixture;

viii. optionally identifying a further subset of synergistic mixtures S(4) by testing one or more of the S(3) mixtures in combination with substantially each component of the library including components that exhibited marginal or no activity in step ii), wherein the concentrations of each of the S(3) components used in the S(4) mixture is the value found in step vii that provides an activity in said assay of $\lambda$ $C_{Max,1}$, with the proviso that some components of the S(3) mixture may be eliminated from this testing step if they are deemed marginally effective in the S(3) ternary mixture when tested in step vii;

ix optionally carrying out a Multi-Component Scaling Protocol on further one or more S(N-1) mixtures that display significant activity in the assay, said mixtures being identified in an analogous fashion to step viii, wherein the concentration of each component of the one or more S(N-1) mixtures is independently varied and the activity of the mixture is measured in the Multi-Pathway High Throughput Assay and determining concentrations for each of the components of the one or more S(N-1) mixtures at which the activity of said S(N-1) mixture in said assay is $\lambda$ $C_{Max,1}$ and determining whether any component of each S(N-1) mixture may be eliminated in further testing cycles because its has become marginally effective in the S(N-1) mixture, wherein N is an integer greater than 4;

x) optionally identifying a further subset of synergistic mixture S(N) by testing one or more of the S(N-1) mixtures in combination with substantially each component of the library including components that exhibited marginal or no activity in step ii), wherein the concentrations of each of the S(N-1) components used in the S(N) mixture is the value found in step ix that provides an activity in said assay of $\lambda$ $C_{Max,1}$, with the proviso that some components of the S(N-1) mixture may be eliminated from this testing step if they are deemed marginally effective in the S(N-1) mixture when tested in step ix.

2. The method according to claim 1 wherein the subsets of S(1) through S(N) tested in combinations with members of the library contain only one or a small number of the components.

3. The method according to claim 1 or 2 wherein the library of potential actives comprises actives selected from the European EINECS list.

4. The method according to claim 1 wherein the library of potential active ingredients comprises ingredients selected from the Cosmetics, Toiletries and Fragrance Association Dictionary of Compounds.

5. The method of claim 4 wherein the library of potential active ingredients is a subset of the Cosmetics, Toiletries and Fragrance Association Dictionary of Compounds selected on the basis of being reported in that volume as having biological activity.

6. The method according to claim 1 wherein the library of potential active ingredients comprises ingredients selected from at least two of the classes selected from the group consisting of retinol and its esters, retinol boosters, short peptides with or without hydrophobic modification or complexation with copper, minoxidil, natural products providing hypertensive activity, natural products containing antiandrogens, and chemicals capable of binding to the vitamin D receptor.

7. The method according to claims 1 wherein the Multi-Pathway High Throughput Assay targets the biological end effect of hair growth.

8. The method according to claim 7 wherein the Multi-Pathway High Throughput Assay is the Isolated Hair Follicle Assay said assay comprising a multiplicity of cultures of individual hair follicles contained in a suitable growth medium wherein said follicles are removed from sectioned dermis in a viable state through the action of collagenase, and wherein hair growth is measured by a high throughput hair growth measurement technique which is not affected by the presence of contaminating tissues in the culture.

9. The method according to claim 8 wherein the high throughput hair growth measurement technique comprises the visualization of an incorporated fluorescent agent in the growing hair.

10. The method according to claim 7 wherein the Multi-Pathway High Throughput Assay is the Low Temperature Whole Skin Organ Culture Assay, said assay comprising a multiplicity of miniaturized cultures of skin maintained in a serum free growth medium at a temperature below about 30, wherein said skin contains intact viable hair follicles below the sebaceous gland, and wherein hair growth is measured by a high-throughput measurement technique.

11. The method according to claim 10 wherein the high throughput hair growth measurement technique comprises the visualization of an incorporated fluorescent agent in the growing hair.

12. The method according to claim 1 wherein the Multi-Pathway High Throughput Assay targets the biological effect of skin anti-aging.

13. The method according to claim 12 wherein the Multi-Pathway High Throughput Assay is the High Throughput Histology Organ Culture Assay said assay comprising the steps of simultaneously treating with test agents viable cultures of pieces of epidermis having at least a portion of their associated dermis intact, said pieces of epidermis contained in a multiple well assembly, wherein said treatment is followed by the embedding of large numbers of cultured skin pieces in a single block and histological sectioning of the entire assembly and the automated histology, histochemistry or immunohistochemisty of histological sections carried out in a high throughput manner.

14. The method according to claim 12 wherein the Multi-Pathway High Throughput Assay is the Topical Application High Throughput Histology Organ Culture Assay said assay comprising a culture of a sheet of viable epidermis and associated dermis, partitioned by the application of a surface barrier film into a pattern of isolated regions to which different test samples can be topically applied, followed after said treatment by the embedding of large numbers of cultured skin pieces in a single block and histological sectioning of the entire assembly and the automated histology, histochemistry or immunohistochemisty of histological sections carried out in a high throughput manner.

15. The method according to claim 1 Wherein the Multi-Pathway High Throughput Assay identifies one or more compounds that ameliorate of acne.

16. The method of claim 15 where the Multi-Pathway High Throughput Assay is the Simulated Follicle P. Acnes Assay said assay comprising a culture of P. Acnes dispersed in a synthetic analogue of human sebum and held in an assembly comprising pieces of tubing of dimensions similar to the sebaceous duct, said assembly being exposed to antibacterial agents under realistic conditions and wherein growth of the surviving P. Acnes is measured by a high throughput measurement technique.

17. The method of claim 15 where the Multi-Pathway High Throughput Assay is the Inhibition of IL1-Induced Hypercornification Assay said assay comprising:
   i) forming a viable culture of pieces of epidermis with at least a portion of associated dermis using a culture medium containing a level of IL1 sufficient to cause hypercornification;
   ii) topically applying to the epidermis the ingredient or ingredients to be tested;
   iii) embedding the cultured pieces of epidermis in a single block;
   iv) sectioning the single block into histological sections;
   v) carrying out automated high throughput assays of histology, histochemistry or immunohistochemisty of the histological sections; and
   vi) determining the extent of reduction of IL1 induced hypercornification by the topically applied ingredient or ingredients.

18. The method according to claim 1 wherein the Multi-Pathway High Throughput Assay targets the biological end effect of dental plaque control.

19. The method according to claim 18 wherein the Multi-Pathway High Throughput Assay is the Plaque Biofilm Regrowth Assay said assay comprising the growth of a plaque biofilm in multiwell plates under conditions of medium replenishment approximately simulating chemostat conditions, followed by the partial removal of the biofilm using mechanical abrasion in the presence of the test agents and detection of the rate of regrowth of the biofilm, optionally using a disclosing agent, via automated image detection.

20. The method according to claim 1 wherein the Multi-Pathway High Throughput Assay targets the biological end effect of microbial growth inhibition or control.

21. The method according to claims 1 wherein the Multi-Pathway High Throughput Assay targets the biological end effect of skin pigmentation control.

22. The method according to claims 1 wherein the Multi-Pathway High Throughput Assay targets the biological end effect of sebum control.

23. The method according to claim 1 wherein the Multi-Pathway High Throughput Assay targets the biological end effect of dandruff control.

24. The method according to claim 1 wherein $\lambda$ is less than or equal to 0.2.

25. The method according to claim 1 wherein $\lambda$ is less than or equal to 0.1.

26. The method according to claim 1 wherein N is an integer between 5 and 10.

* * * * *